United States Patent [19]
Wiezer et al.

[11] 4,191,684
[45] Mar. 4, 1980

[54] UREA DERIVATIVES, THEIR PREPARATION, AND THEIR USE AS LIGHT STABILIZERS

[75] Inventors: Hartmut Wiezer, Gersthofen; Gerhard Pfahler, Augsburg; Norbert Mayer; Harald Knorr, both of Gersthofen, all of Fed. Rep. of Germany

[73] Assignee: Hoechst Aktiengesellschaft, Frankfurt am Main, Fed. Rep. of Germany

[21] Appl. No.: 935,470

[22] Filed: Aug. 21, 1978

[30] Foreign Application Priority Data
Aug. 25, 1977 [DE] Fed. Rep. of Germany ....... 2738340

[51] Int. Cl.² ................ C07D 491/10; C07D 491/20; C08K 5/35
[52] U.S. Cl. ...................... 260/48.5 NT; 260/45.8 N; 260/45.8 NZ; 546/19
[58] Field of Search ............... 260/45.8 NT, 45.8 NZ; 546/19

[56] References Cited
U.S. PATENT DOCUMENTS
4,107,139  8/1978  Mayer et al. .......................... 546/19

OTHER PUBLICATIONS
Noller "Chemistry of Organic Compounds" 2nd ed., (Saunders) (1957), p. 317.

*Primary Examiner*—Alan L. Rotman
*Assistant Examiner*—Robert T. Bond
*Attorney, Agent, or Firm*—Connolly and Hutz

[57] ABSTRACT

The invention provides novel 4-carbamoyl derivatives of 1-oxa-3-oxo-4,8-diaza-spiro-[4,5]-decanes and their preparation from 1 oxa-3-oxo-4,8-diaza-spiro-[4,5]-decanes and isocyanates. The products are suitable light stabilizers for thermoplastics.

5 Claims, No Drawings

UREA DERIVATIVES, THEIR PREPARATION, AND THEIR USE AS LIGHT STABILIZERS

The present invention provides novel urea derivatives, the preparation thereof and their use as stabilizers for synthetic polymers.

The novel urea derivatives are compounds of the formula (I)

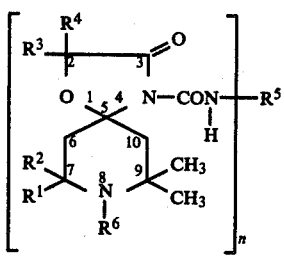

in which $R^1$ and $R^2$, being identical or different, each are linear or branched alkyl radicals having from 1 to 12, preferably 1 to 6, carbon atoms, especially methyl groups, or $R^1$ and $R^2$ together with the carbon atom to which they are lined form an optionally methyl-substituted cyclopentane or cyclohexane ring or a 2,2,6,6-tetramethylpiperidine ring the carbon atom 4 of which is identical with the carbon atom 7 of the spirodecane system, preferably the latter ring;

is hydrogen, an alkyl or isoalkyl radical having from 1 to 30, preferably 1 to 10, and especially 1 to 6, carbon atoms, or an aralkyl radical having from 7 to 10 carbon atoms, the aliphatic chain having from 1 to 4 carbon atoms;

is hydrogen, an alkyl group having from 1 to 30, preferably 1 to 17, and especially 1 to 11, carbon atoms, an aryl radical having 6 or 10 carbon atoms, optionally substituted by a halogen atom, preferably chlorine, or an alkyl radical having from 1 to 4 carbon atoms, or an aralkyl radical having from 7 to 10 carbon atoms, the aliphatic chain containing from 1 to 4 of the latter carbon atoms; or $R^3$ and $R^4$ together with the carbon atom linking them form a cycloalkane ring having from 4 to 20, preferably from 5 to 12, and especially 5 to 7, carbon atoms, the cycloalkane ring optionally being substituted by $C_1$–$C_4$-alkyl radicals;

$R^5$, when n is 1, is an alkyl group having from 1 to 20, preferably 4 to 18, carbon atoms, an alkenyl group having from 3 to 18 carbon atoms, a cycloalkyl radical having from 5 to 12, preferably 5 to 7, and especially 6, carbon atoms, optionally substituted by a $C_1$–$C_4$-alkyl radical, an aryl radical having 6 to 10 carbon atoms optionally substituted by a chlorine atom or an alkyl radical having from 1 to 18, preferably 1 to 4, carbon atoms, or an aralkyl radical having from 7 to 18, preferably 7 to 10, carbon atoms, the aryl ring containing 6 carbon atoms;

$R^5$, when n is 2, is linear or branched alkylene having from 2 to 20, preferably 2 to 12, and especially 2 to 6, carbon atoms, arylene having 6 or 10 carbon atoms optionally substituted by $C_1$–$C_4$-alkyl, or aralkylene having from 7 to 18 carbon atoms; and $R^6$ is hydrogen, oxygen, hydroxyl or an alkyl radical having from 1 to 4 carbon atoms, preferably hydrogen or methyl, especially hydrogen.

Since the nitrogen atom 8 has basic properties when it is substituted by H or alkyl, the compounds may be present in these cases also in the form of salts of organic or inorganic acids.

Examples for $R^1$ and $R^2$ are methyl, ethyl, i-butyl, and for the case where $R^1$ and $R^2$ together with the carbon atom to which they are linked form a ring: cyclopentyl, cyclohexyl or 2,2,6,6-tetramethylpiperidyl.

Examples for $R^3$ are hydrogen, methyl, ethyl, propyl, butyl, pentyl, hexyl, heptyl, benzyl, for R4: hydrogen, methyl, ethyl, propyl, isopropyl, butyl, isobutyl pentyl, isopentyl, hexyl, isohexyl, heptyl, isoheptyl, octyl, iso-octyl, nonyl, isononyl, decyl, isodecyl, undecyl, dodecyl, tridecyl, benzyl, phenyl, chlorophenyl, phenylethyl.

Examples of those cases where $R^3$ and $R^4$ together with the ring carbon atom 2 to which they are linked form a cycloalkyl ring are cyclopentyl, cyclohexyl, methylcyclohexyl, cycloheptyl or cyclododecyl.

Examples of $R^5$ in compounds where n is 1 are radicals of mono-isocyanates such as methyl, ethyl, propyl, butyl, isobutyl, octadecyl, cyclohexyl, phenyl, 3-chlorophenyl, 4-chlorophenyl, 3-methylphenyl, 4-methylphenyl, 1-naphthyl.

When n is 2, $R^5$ is the radical of a diisocyanate, for example ethylene, hexamethylene, diphenylenemethane. 4-methyl-m-phenylene.

Examples of $R^6$ are hydrogen or lower alkyl, especially methyl.

Examples of possible salts of compounds of the formula I are those with inorganic acids such as phosphates, phosphites, chlorides, sulfates, or salts with organic mono- and polycarboxylic acids such as acetates, laurates, stearates, succinates, sebacates, maleates, citrates, tartrates, oxalates, benzoates, sulfonates or phosphonates etc..

Examples of compounds of the formula I are the following:

2,2,7,7,9,9-hexamethyl-4-α-naphthyl-carbamoyl-1-oxa-3-oxo-4,8-diaza-spiro-[4,5]-decane;

2,2,7,7,9,9-hexamethyl-4-cyclohexyl-carbamoyl-1-oxa-3-oxo-4,8-diaza-spiro-[4,5]-decane;

2,2,7,7,9,9-hexamethyl-4-phenyl-carbamoyl-1-oxa-3-oxo-4,8-diaza-spiro-[4,5]-decane;

2,2,7,7,9,9-hexamethyl-4-octadecyl-carbamoyl-1-oxa-3-oxo-4,8-diaza-spiro-[4,5]-decane;

diphenylene-methane-4',4''-bis-(4-carbamoyl-2,2,7,7,9,9-hexamethyl-1-oxa-3-oxo-4,8-diaza-spiro-[4,5]-decane);

n-hexane-1',6'-bis-(4-carbamoyl-2,2,7,7,9,9-hexamethyl-1-oxa-3-oxo-4,8-diaza-spiro-[4,5]-decane);

n-hexane-1',6'-bis-(4-carbamoyl-2,7,7,9,9-pentamethyl-2-propyl-1-oxa-3-oxo-4,4-diaza-spiro-[4,5]-decane);

2,7,7,9,9-pentamethyl-2-iso-butyl-4-phenyl-carbamoyl-1-oxa-3-oxo-4,8-diaza-spiro-[4,5]-decane;

diphenylene-methane-4',4''-bis-(4-carbamoyl-2,7,7,9,9-pentamethyl-2-pentyl-1-oxa-3-oxo-4,8-diaza-spiro-[4,5]-decane);

n-hexane-1',6'-bis-(4-carbamoyl-2,7,7,9,9-pentamethyl-2-hexyl-1-oxa-3-oxo-4,8-diaza-spiro-[4,5]-decane);

n-hexane-1',6'-bis-(4-carbamoyl-2,2-diethyl-7,7,9,9-tetramethyl-1-oxa-3-oxo-4,8-diaza-spiro-[4,7]-decane);

2,2-dipropyl-7,7,9,9-tetramethyl-4-octadecyl-carbamoyl-1-oxa-3-oxo-4,5-diaza-spiro-[4,5]-decane;

2-propyl-7,7,9,9-tetramethyl-4-propyl-carbamoyl-1-oxa-3-oxo-4,8-diaza-spiro-[4,5]-decane;
2-iso-butyl-7,7,9,9-tetramethyl-4-cyclohexyl-carbamoyl-1-oxa-3-oxo-4,8-diaza-spiro-[4,5]-decane;
n-hexane-1',6'-bis-(4-carbamoyl-2-iso-butyl-7,7,9,9-tetramethyl-1-oxa-3-oxo-4,8-diaza-spiro-[4,5]-decane);
n-hexane-1',6'-bis-(4-carbamoyl-2-iso-pentyl-7,7,9,9-tetramethyl-1-oxa-3-oxo-4,8-diaza-spiro-[4,5]-decane).

The novel compounds of the formula (I) are obtained by reaction of isocyanates or diisocyanates (II) with piperidines of the formula (III) which are prepared according to the indications of German Offenlegungsschrift No. 2,634,957. The reaction proceeds according to the following scheme:

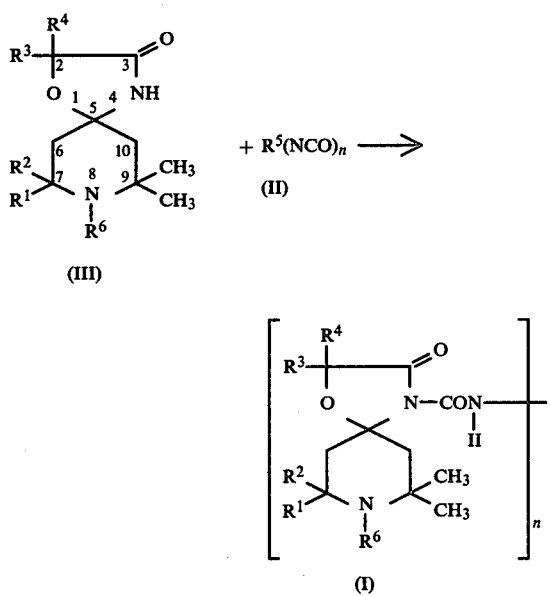

in which $R^1$ to $R^6$ are as defined above, n is 1 or 2 depending on the functionality of the isocyanate. Especially surprising in this reaction is the fact that even those compounds of formula (III) in which $R^6$ is hydrogen react with isocyanates in the cited manner and not at the amino-nitrogen in 8-position.

The reaction is carried out as follows: the piperidine derivative in an inert organic solvent is introduced into the reactor, a catalytic amount of a strong base, for example 1,4-di-azabicyclo-octane, is added, the equivalent amount of the isocyanate, optionally dissolved in the same solvent, is added dropwise, and the reaction is allowed to proceed at a temperature of from 20° to 180°, preferably 20° to 140°, and especially 50° to 120° C. The reaction time is from 1 to 30, preferably 4 to 20, hours.

Suitable inert solvents are for example heptane, aliphatic hydrocarbon fractions having boiling ranges of up to 180° C., toluene, xylene, diethyl ether, dioxan, halogenated hydrocarbons such as chloroform, carbon tetrachloride, chlorobenzene; preferably toluene.

Scarcely soluble reaction products are separated by filtration, while soluble ones remaining in dissolved state are purified by recrystallization after evaporation of the solvent.

The novel urea derivatives are excellently suitable for stabilizing synthetic polymers against the decomposing effect of light.

By synthetic polymers, there are to be understood in this connection halogen-free and halogen-containing homo- and copolymers, in particular homopolymers of olefins, dienes and styrene, for example polyethylene of low and high density, polypropylene, polystyrene, polybutadiene and polyisoprene, copolymers of olefins, dienes, and styrene with one another or with other olefinically unsaturated monomers, such as ethylene-propylene copolymers, ethylene-butene copolymers, styrene-butadiene copolymers, ethylene-vinyl acetate copolymers and acrylonitrile-butadiene-styrene copolymers, homopolymers of vinyl chloride and vinylidene chloride and copolymers of these monomers with one another and with other olefinically unsaturated monomers. There are also to be included polyurethanes, polyacetals, polyesters, polyamides, polyacrylates, and epoxy resins. Preference is given to poly-α-olefins, such as polyethylenes and especially polypropylenes, as well as to the polymers of vinyl chloride.

It was surprising and not to be expected that the products of the invention are considerably superior with respect to their UV stabilizing effect to the compounds having comparable structural characteristics, that is, ureas or spirodecanes of a similar basis framework, described in German Offenlegungsschriften Nos. 2,500,313, 1,770,689 and 1,769,646. For, since the structural modifications were supposed to be rather insignificant, it could be assumed that the effect of the compounds of the invention would be the same or even less, because their polarity would suggest a reduced compatibility especially with unpolar polymers, for example polyolefins.

The stabilizers according to the invention are incorporated into the polymer compositions according to methods that are generally common. Alternatively, it is also possible to mix a solution, suspension or emulsion of the stabilizer directly with the polymer, or with a solution, suspension or emulsion of the same, and to eliminate the solvent thereafter.

The stabilizers of the invention may be used alone or in admixture with one or several of the stabilizers which are common in the processing of plastic materials, such as antioxidants on the basis of phenol and sulfide, UV-absorbers and light protecting agents, phosphite stabilizers, metal compounds, epoxy stabilizers and polyhydric alcohols. In the plastic composition to be stabilized there may also be present flame-proofing agents and pigments, dyestuffs, antistatic agents and fillers, such as glass fibers.

Examples for appropriate antioxidants are those of the type of the sterically hindered phenols, such as 2,6-di-t.-butyl-p-cresol, 2,6-di-octadecyl-p-cresol, 4,4'-butylidene-bis-(2,6-di-t.-butyl-phenol), 4,4'-thio-bis(2-t.-butyl-5-methyl-phenol), phenolic triazine compounds, thiodipropionic acid esters of fatty alcohols, dioctadecyl sulfide and -disulfide.

The UV-absorbers and light protecting agents include, for example, 2-(2'-hydroxyphenyl)-benzotriazoles, such as 2-(2'-hydroxy-5'-methylphenyl)-benzotriazole, 2-hydroxybenzophenones, such as 2-hydroxy-4-octoxy-benzophenone, stabilizers of the group of the salicylates, such as octylphenyl salicylate, nickel chelates, oxalic acid diamides and sterically hindered piperidine compounds.

As phosphites there are to be mentioned trisnonylphenyl phosphite, trislauryl phosphite or esters of pentaerythritol phosphite.

By metal compounds known as stabilizers there are to be understood in this respect: Calcium, barium, strontium, zinc, cadmium, magnesium, aluminum and lead soaps of aliphatic carboxylic acids or hydroxycarboxylic acids having from about 12 to 32 carbon atoms, salts of the aforesaid metals with aromatic carboxylic acids, such as benzoates or salicylates, and (alkyl-)phenolates of these metals, and also organo-tin compounds such as, for example, dialkyltin thioglycolates and carboxylates.

Known epoxy-stabilizers are, for example, epoxidized higher fatty acids, such as epoxidized soy bean oil, tall oil, linseed oil or epoxidized butyl oleate, and also epoxides of long-chain olefins.

Polyhydric alcohols may be, for example, pentaerythritol, trimethylolpropane, sorbitol or mannitol, i.e. preferably alcohols having 5 or 6 carbon atoms and from 3 to 6 OH-groups.

An effective stabilizer combination for poly- -olefins such as, for example, high, medium and low pressure polymers of $C_2$- to $C_4$-$\alpha$-olefins, especially polyethylene and polypropylene or copolymers of such $\alpha$-olefins, consists, calculated on 100 parts by weight of polymer, for example, of from 0.01 to 5 parts by weight of one of the compounds to be used in accordance with the invention, of from 0.005 to 5 parts by weight of a phenolic stabilizer, optionally of from 0.01 to 5 parts by weight of a sulfur-containing costabilizer, and optionally of from 0.01 to 3 parts by weight of a basic or neutral metal soap such as, for example, calcium stearate or zinc stearate, and optionally of from 0.1 to 5 parts by weight weight of a phosphite and optionally of from 0.01 to 5 parts by weight of a known UV-stabilizer of the group of alkoxy-hydroxy-benzophenones, hydroxyphenyl-benzotriazoles, benzylidene-malonic acid-mononitrile esters or the so called quenchers, such as nickel chelates.

The following Examples serve to illustrate the invention. The structure of the compounds were determined by nuclear resonance spectroscopy.

EXAMPLE 1

2,2,7,7,9,9-hexamethyl-4-$\alpha$-naphthyl-carbamoyl-1-oxa-3-oxo-4,8-diaza-spiro-[4,5]-decane 12.0 g (0.05 mol) 2,2,7,7,9,9.-hexamethyl-1-oxa-3-oxo-4,8-diaza-spiro-[4,5]-decane, 8.5 g (0.05 mol) naphthyl-1-isocyanate, 0.1 g 1,4-diazabicyclooctane and 100 ml absolute toluene were refluxed for 15 hours with agitation. Subsequently, the toluene was distilled off and the residue recrystallized from heptane. M.p. 158° C.

EXAMPLES 2 to 16

According to the indications of Example 1, the following compounds were prepared:

| Example No. | Compound /m.p./ starting material |
|---|---|
| 2 | 2,2,7,7,9,9-hexamethyl-4-cyclohexyl-carbamoyl-1-oxa-3-oxo-4,8-diaza-spiro-[4,5]-decane (m.p. 148° C.) from 2,2,7,7,9,9-hexamethyl-1-oxa-3-oxo-4,8-diaza-spiro-[4,5]-decane and $C_6H_{11}NCO$ |
| 3 | 2,2,7,7,9,9-hexamethyl-4-phenyl-carbamoyl-1-oxa-3-oxo-4,8-diaza-spiro-[4,5]-decane (m.p. 174° C.) from 2,2,7,7,9,9-hexamethyl-1-oxa-3-oxo-4,8-diaza-spiro-[4,5]-decane and $C_6H_5NCO$ |
| 4 | 2,2,7,7,9,9-hexamethyl-4-octadecyl-carbamoyl-1-oxa-3-oxo-4,8-spiro-[4,5]-decane (m.p. 65° C.) from 2,2,7,7,9,9-hexamethyl-1-oxa-3-oxo-4,8-diaza-spiro-[4,5]-decane and $C_{18}H_{37}NCO$ |
| 5 | diphenylene-methane-4',4''-bis-(4-carbamoyl-2,2,7,7,9,9-hexamethyl-1-oxa-3-oxo-4,8-diaza-spiro-[4,5]-decane (m.p. 287° C.) from 2,2,7,7,9,9-hexamethyl-1-oxa-3-oxo-4,8-diaza-spiro-[4,5]-decane and $CH_2(C_6H_4NCO)_2$ |
| 6 | n-hexane-1',6'-bis-(4-carbamoyl-2,2,7,7,9,9-hexamethyl-1-oxa-3-oxo-4,8-diaza-spiro-[4,5]-decane (183°–186° C.) from 2,2,7,7,9,9-hexamethyl-1-oxa-3-oxo-4,8-diaza-spiro-[4,5]-decane and $(CH_2)_6(NCO)_2$ |
| 7 | 2,7,7,9,9-pentamethyl-2-iso-butyl-4-phenyl-carbamoyl-1-oxa-3-oxo-4,8-diaza-spiro-[4,5]-decane (86°–88° C.) from 2,7,7,9,9-pentamethyl-2-iso-butyl-1-oxa-3-oxo-4,8-diaza-spiro-[4,5]-decane and $C_6H_5NCO$ |
| 8 | Diphenylene-methane-4',4''-bis-(4-carbamoyl-2,7,7,9,9-pentamethyl-2-pentyl-1-oxa-3-oxo-4,8-diaza-spiro-[4,5]-decane (298° C.) from 2,7,7,9,9-pentamethyl-2-pentyl-1-oxa-3-oxo-4,8-diaza-spiro-[4,5]-decane and $CH_2(C_6H_4)_2(NC0)_2$ |
| 9 | n-Hexane-1',6'-bis-(4-carbamoyl-2,2-diethyl-7,7,9,9-tetramethyl-1-oxa-3-oxo-4,8-diaza-spiro-[4,5]-decane) (117° C.) from 2,2-diethyl-7,7,9,9-tetramethyl-1-oxa-3-oxo-4,8-diaza-spiro-[4,5]-decane and $(CH_2)_6(NCO)_2$ |
| 10 | n-Hexane-1',6'-bis-(4-carbamoyl-2,7,7,9,9-penta-methyl-2-hexyl-1-oxa-3-oxo-4,8-diaza-spiro-[4,5]-decane (116°–118° C.) from 2,7,7,9,9-pentamethyl-2-hexyl-1-oxa-3-oxo-4,8-diaza-spiro-[4,5]-decane and $(CH_2)_6(NCO)_2$ |
| 11 | 2,2-Dipropyl-7,7,9,9-tetramethyl-4-octadecyl-carbamoyl-1-oxa-3-oxo-4,8-diaza-spiro-[4,5]-decane (85°–90° C.) from 2,2-dipropyl-7,7,9,9-tetramethyl-1-oxa-3-oxo-4,8-diaza-spiro-[4,5]-decane and $C_{18}H_{37}NCO$ |
| 12 | 2-Propyl-7,7,9,9-tetramethyl-4-propyl-carbamoyl-1-oxa-3-oxo-4,8-diaza-spiro-[4,5]-decane (66° C.) from 2-propyl-7,7,9,9-tetramethyl-1-oxa-3-oxo-4,8-diaza-spiro-[4,5]-decane and $C_3H_7NCO$ |
| 13 | 2-iso-Butyl-7,7,9,9-tetramethyl-4-cyclohexyl-carbamoyl-1-oxa-3-oxo-4,8-diaza-spiro-[4,5]-decane (150° C.) from 2-iso-butyl-7,7,9,9-tetra-methyl-1-oxa-3-oxo-4,8-diaza-spiro-[4,5]-decane and $C_6H_{11}NCO$ |
| 14 | n-Hexane-1',6'-bis-(4-carbamoyl-2,7,7,9,9-penta-methyl-2-propyl-1-oxa-3-oxo-4,8-diaza-spiro-[4,5]-decane) (80°–85° C.) from 2,7,7,9,9-pentamethyl-2-propyl-1-oxa-3-oxo-4,8-diaza-spiro-[4,5]-decane and $(CH_2)_6(NCO)_2$ |
| 15 | n-Hexane-1',6'-bis-(4-carbamoyl-2-iso-butyl-7,7,9,9-tetramethyl-1-oxa-3-oxo-4,8-diaza-spiro-[4,5]-decane) (115°–117° C.) from 2-iso-butyl-7,7,9,9-tetramethyl-1-oxa-3-oxo-4,8-diaza-spiro-[4,5]-decane and $(CH_2)_6(NCO)_2$ |
| 16 | n-Hexane-1',6'-bis-(4-carbamoyl-2-iso-pentyl-7,7,9,9-tetramethyl-1-oxa-3-oxo-4,8-diaza-spiro-[4,5]-decane (109° C.) from 2-iso-pentyl-7,7,9,9-tetramethyl-1-oxa-3-oxo-4,8-diaza-spiro-[4,5]-decane and $(CH_2)_6(NCO)_2$. |

EXAMPLE 17

This example demonstrates the light stabilizing action of the compounds of the invention when applying them to a poly-alpha-olefin.

100 parts by weight of polypropylene having a melt flow index i$_5$ of about 6 g/10 min. (determined according to ASTM D 1238-62 T) and a density of 0.96, were mixed with 0.1 part by weight of pentaerythrityl-tetrakis-[3-(3,5-di-tert.-butyl-4-hydroxyphenyl)-propionate], 0.2 part by weight of calcium stearate and 0.1 part by weight of the stabilizer of the invention to be tested.

In order to obtain a uniform distribution on the polymer grain, the stabilizers were dissolved in a solvent, and the solution was added dropwise with agitation to the polypropylene powder, while simultaneous radiation by means of an IR lamp ensured substantial evaporation of the solvent. After about 20 minutes, the calcium stearate was added, and the batch was mixed for a further 10 minutes. The solvent remainder was removed by drying in a drying cabinet at 50° C. for 120 minutes.

On a Windsor injection molding machine type SP 50, plates having the dimensions of 60×60×1 mm were molded at 250° C. from the above material, and test specimens according to German Industrial Standard DIN 53 455, form 3, in a scale reduced at a 1:3 ratio, were cut from these plates. The test specimens required as comparative samples were prepared and formed in analogous manner, while omitting either the stabilizer to be tested (Test g) or using known light stabilizers (Tests e and f).

The stability to light was tested according to German Industrial Standard DIN 53 387 (accelerated test of weathering-resistance) using a ®Xenotest 450 apparatus of the company Original Hanau Quarzlampen GmbH and the filter combination 6 IR+1 UV. During the time of exposure, the blackpanel temperature was 43°±1° C., and the relative atmospheric moisture in the test chamber was 70%±1%. Fresh air was passed through the test chamber for 5 minutes every 2 hours. After a defined time of exposure, the elongation at break was determined on a tensile testing machine of the Instron company at a draw-off speed of 5 cm/min. The results are listed in the following Table.

The stabilizing factor follows from the ratio of radiation time of the stabilized test specimens to the radiation time of the non-stabilized test specimens; the radiation being continued in all cases until the elongation at break had dropped to half the starting value.

As results from the Table, the stabilizing effect is better than that of a benzophenone or benzotriazole stabilizer. It is also better than that of n-hexane-1,6-bis(1,4-carbamoyl-7,14-diaza-dispiro-[5,1,5,2]-pentadecan-15-one), the product according to Example 3 of German Offenlegungsschrift No. 2,500,313 which, as shows the Test Example 11 of the cited patent application, had only a factor of 3.1.

| Test No. | Stabilizer acc. to Example | Stabilizing factor |
|---|---|---|
| (a) | 4 | >5 |
| (b) | 6 | >5 |
| (c) | 10 | >5 |
| (d) | 15 | >5 |
| (e) | Benzophenone stabilizer[1] | <2.5 |
| (f) | Benzotriazole stabilizer[2] | <2.1 |
| (g) | Control (without stabilizer) | 1 |

[1]2-Hydroxy-4-n-octyloxybenzophenone
[2]2-(2-Hydroxy-3′,5′-di-tert.-butylphenyl)-5-chlorobenzotriazole

What is claimed is:

1. A compound of the formula (I)

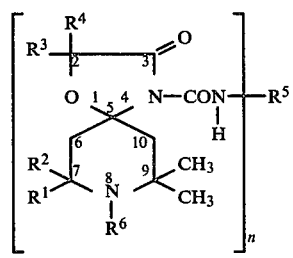

in which $R^1$ and $R^2$, being identical or different, each are linear or branched alkyl having from 1 to 12 carbon atoms, or $R^1$ and $R^2$ together with the carbon atom to which they are linked form a cyclopentane or cyclohexane ring which may also be methyl-substituted or a 2,2,6,6-tetramethylpiperidine ring the carbon atom 4 of which is identical with the carbon atom 7 of the spirodecane system;

$R^3$ is hydrogen, alkyl or isoalkyl having from 1 to 30 carbon atoms, or phenylalkyl having from 7 to 10 carbon atoms, the aliphatic chain having from 1 to 4 carbon atoms;

$R^4$ is hydrogen, alkyl having from 1 to 30 carbon atoms, phenyl or naphthyl, which may be substituted by a halogen atom, or alkyl radical having from 1 to 4 carbon atoms, or phenylalkyl having from 7 to 10 carbon atoms, the aliphatic chain containing from 1 to 4 of the latter carbon atoms; or $R^3$ and $R^4$ together with the carbon atom linking them form a cycloalkane ring having from 4 to 20 carbon atoms;

$R^5$, when n is 1, is alkyl having from 1 to 20 carbon atoms, alkenyl having from 3 to 18 carbon atoms, cycloalkyl having from 5 to 12 carbon atoms, which may be substituted by $C_1$–$C_4$-alkyl phenyl or naphthyl which may be substituted by a chlorine atom or alkyl having from 1 to 18 carbon atoms, or phenylalkyl having from 7 to 18 carbon atoms, the aryl ring containing 6 carbon atoms;

$R^5$, when n is 2, is linear or branched alkylene having from 2 to 20 carbon atoms, phenylene or naphthylene which may be substituted by $C_1$–$C_4$-alkyl, or phenylalkylene having from 7 to 18 carbon atoms; and $R^6$ is hydrogen, oxygen, hydroxyl or alkyl having from 1 to 4 carbon atoms.

2. A compound as claimed in claim 1, in which $R^1$ and $R^2$ are methyl and $R^6$ is hydrogen.

3. A process for the preparation of a compound as claimed in claim 1 or 2, which comprises reacting a compound of the formula (III)

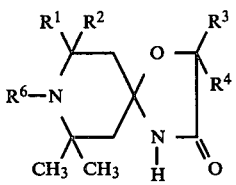

with an isocyanate of the formula (II)

in which formula $R^1$ to $R^6$ are as defined in claim 9, in and inert organic solvent at temperatures of from 20° to 180° C. with addition of catalytic amounts of a base.

4. Process for stablizing halogen-free aliphatic alpha-olefin homo- and copolymers and chlorine-containing vinyl homo- and copolymers against the damaging influence of light, wherein 0.01 to 5 parts by weight, based on the polymer, of a compound of claim 1 or a salt thereof with an inorganic or organic acid, is added to the polymers.

5. Organic polymers stablized against UV decomposition, containing 0.01 to 5 parts by weight, calculated on the polymers, of a compound as claimed in claim 1 or of a salt thereof with an inorganic or organic acid.

* * * * *